US012793212B2

(12) United States Patent
Potter et al.

(10) Patent No.: US 12,793,212 B2
(45) Date of Patent: Nov. 10, 2026

(54) AUTOMATED AND RAPID DETECTION AND LOCALIZATION OF FREE FLUID ON FOCUSED ASSESSMENT WITH SONOGRAPHY IN TRAUMA (FAST) EXAMINATION USING DEEP LEARNING

(71) Applicant: BioSensics LLC, Newton, MA (US)

(72) Inventors: Ilkay Yildiz Potter, Boston, MA (US); Ashkan Vaziri, Newton, MA (US)

(73) Assignee: BioSensics LLC, Newton, MA (US)

( * ) Notice: Subject to any disclaimer, the term of this patent is extended or adjusted under 35 U.S.C. 154(b) by 211 days.

(21) Appl. No.: 18/391,383

(22) Filed: Dec. 20, 2023

(65) Prior Publication Data

US 2024/0212138 A1 Jun. 27, 2024

Related U.S. Application Data

(60) Provisional application No. 63/476,538, filed on Dec. 21, 2022.

(51) Int. Cl.
*G06T 7/00* (2017.01)
*G16H 30/20* (2018.01)

(52) U.S. Cl.
CPC ........... *G06T 7/0012* (2013.01); *G16H 30/20* (2018.01); *G06T 2200/24* (2013.01); *G06T 2207/10016* (2013.01); *G06T 2207/10132* (2013.01); *G06T 2207/20081* (2013.01); *G06T 2207/20084* (2013.01); *G06T 2207/30048* (2013.01); *G06T 2210/12* (2013.01)

(58) Field of Classification Search
None
See application file for complete search history.

(56) References Cited

U.S. PATENT DOCUMENTS

2020/0069292 A1* 3/2020 Abolmaesumi ...... A61B 8/5207
2022/0293243 A1* 9/2022 Callcut .................. G16H 50/20
2023/0038364 A1* 2/2023 Bhowmick ............ G06N 3/045

(Continued)

OTHER PUBLICATIONS

Akkus et al. "A Survey of Deep-Learning Applications in Ultrasound: Artificial Intelligence-Powered Ultrasound for Improving Clinical Workflow" Journal of the American College of Radiology 2019, in 12 pages.

(Continued)

*Primary Examiner* — Helen Zong
(74) *Attorney, Agent, or Firm* — Knobbe, Martens, Olson & Bear, LLP

(57) ABSTRACT

Systems and methods for automated and rapid detection of free fluid. An example method includes obtaining medical images associated with a patient, the medical images being ultrasound images depicting different portions of the patient, and the ultrasound images forming video of the different portions; providing the medical images to a machine learning model, wherein a forward pass through the machine learning model is computed, and wherein the machine learning model is trained to output for each input medical image, a bounding box about free fluid depicted in the input medical image and a confidence score associated with detection of the free fluid in the bounding box; and determining that the patient has free fluid based on analyzing output from the machine learning model.

17 Claims, 17 Drawing Sheets

(56) References Cited

U.S. PATENT DOCUMENTS

2023/0086993 A1* 3/2023 Danielsson ............ G06T 7/136 382/173
2025/0061574 A1* 2/2025 Yao ...................... A61B 3/1225

OTHER PUBLICATIONS

ATLS Subcommittee, "Advanced trauma life support (ATLS®): the ninth edition" American College of Surgeons' Committee on Trauma; and the International ATLS working group. J Trauma Acute Care Surg., 2013, vol. 74 (5), in 4 pages.
Boniface et al., "Tele-ultrasound and paramedics: real-time remote physician guidance of the Focused Assessment With Sonography for Trauma examination" American Journal of Emergency Medicine Jun. 2011;29(5), in 5 pages.
Chaijareenont et al., "FAST accuracy in major pelvic fractures for decision-making of abdominal exploration: Systematic review and meta-analysis" Annals of Medicine Surgery. Oct. 24, 2020;60, in 7 pages.
Cheng et al., "Deep Learning Assisted Detection of Abdominal Free Fluid in Morison's Pouch During Focused Assessment With Sonography in Trauma" Frontiers in Medicine Sep. 23, 2021;8, in 7 pages.
Coley et al. "Focused abdominal sonography for trauma (FAST) in children with blunt abdominal trauma" Journal of Trauma and Acute Care Surgery, 48(5), pp. 902-906, Sep. 2020, in 5 pages.
Dey et al., "On robustness of radial basis function network with input perturbation" Neural Comput & Applic 31, 523-537 (2019), in 15 pages.
Diniz et al., "Deep Learning strategies for Ultrasound in Pregnancy" Eur Med J Reprod Health. Aug. 2020;6(1):73-80. Epub Aug. 25, 2020, in 12 pages.
Drake et al., "Innovations with tele-ultrasound in education sonography: the use of tele-ultrasound to train novice scanners" Ultrasound J. Feb. 14, 2021;13(1):6, in 8 pages.
Ferreira, et al., "Teleultrasound: historical perspective and clinical application" International Journal of Telemedicine and Applications, Feb. 2015. p. 306259, in 12 pages.
Fornari et al., "Pediatric Blunt Abdominal Trauma and Point-of-Care Ultrasound" Pediatric Emergency Care. Dec. 1, 2021;37(12):624-629, in 6 pages.
Gonzales et al. Jun. 2001. TER: a system for robotic tele-echography. Lecture Notes in Computer Science, in 9 pages.
Heegaard, et al., "Prehospital ultrasound by paramedics: results of field trial" Academic Emergency Medicine, 2010. 17(6), in 9 pages.
Ioffe et al., "Batch normalization: Accelerating deep network training by reducing internal covariate shift" International conference on machine learning: PMLR; May 2015, in 9 pages.
Kingma et al., "Adam: A method for stochastic optimization" 2015, in 15 pages.
Kolbe et al., "Point of care ultrasound (POCUS) telemedicine project in rural Nicaragua and its impact on patient management" J Ultrasound, Apr. 2015. 18(2), in 7 pages.
Kornblith et al., "Development and Validation of a Deep Learning Strategy for Automated View Classification of Pediatric Focused Assessment With Sonography for Trauma" J Ultrasound Med. Aug. 2022;41(8), in 17 pages.
Krogh et al., "A simple weight decay can improve generalization" Advances in neural information processing systems. Proceedings of the 4th International Conference on Neural Information Processing Systems, 950-957 (1991), in 8 pages.
Laumer et al., Assessment of Artificial Intelligence in Echocardiography Diagnostics in Differentiating Takotsubo Syndrome From Myocardial Infarction. JAMA Cardiol. May 1, 2022;7(5):494-503, in 23 pages.
Lee et al., "Application of artificial intelligence-based technologies in the healthcare industry: Opportunities and challenges" International Journal of Environmental Research and Public Health, 2021, 18(1), in 18 pages.
Leo et al., "Using Deep Learning to Detect the Presence and Location of Hemoperitoneum on the Focused Assessment with Sonography in Trauma (FAST) Examination in Adults" Journal of Digital Imaging (2023), in 16 pages.
Levine et al., "Tele-intensivists can instruct non-physicians to acquire high-quality ultrasound images" Journal of Critical Care, 2015, in 5 pages.
Lin et al., "Deep learning for emergency ascites diagnosis using ultrasonography images" Journal of Applied Clinical Med Physics. Jul. 2022;23(7): Epub Jun. 20, 2022, in 8 pages.
Lin et al., "Microsoft COCO: Common objects in context" In European Conference on Computer Vision, pp. 740-755. Springer, Cham, 2014, in 16 pages.
Liu et al., "Deep Learning in Medical Ultrasound Analysis: A Review. Engineering" 2019;5(Generic):261-275, in 15 pages.
Liu et al., 2016. SSD: Single shot multibox detector. In Computer Vision—ECCV 2016: 14th European Conference, Amsterdam, The Netherlands, Oct. 11-14, 2016, Proceedings, Part I 14 (pp. 21-37). Springer International Publishing in 17 pages.
McMahon et al. 2020. "Tablet-based limited echocardiography to reduce sonographer scan and decontamination time during the COVID-19 pandemic" Journal of the American Society of Echocardiography, 33(7), in 6 pages.
Melniker et al., "Randomized controlled clinical trial of point-of-care, limited ultrasonography for trauma in the emergency department: the first sonography outcomes assessment program trial" American Emergency Med. Sep. 2006;48(3):227-35, in 9 pages.
Netherton et al., "Diagnostic accuracy of eFAST in the trauma patient: a systematic review and meta-analysis" CJEM. Nov. 2019;21(6):727-738, in 12 pages.
Pearl et al., "Ultrasonography for the initial evaluation of blunt abdominal trauma: A review of prospective trials" Annals of Emergency Medicine. Mar. 1996;27(3):353-61, in 9 pages.
Pedregosa et al., "Scikit-learn: Machine learning in Python" Journal of machine Learning research 2011, in 6 pages.
Pokaprakarn et al., "AI Estimation of Gestational Age from Blind Ultrasound Sweeps in Low-Resource Settings" NEJM Evidence Mar. 28, 2022;1(5), in 11 pages.
Power et al., "Principles for high-quality, high-value testing" BMJ Evidence-Based Medicine 18, No. 1 (2013): 5-10, in 6 pages.
Qi et al., "Focused Assessment with Sonography in Trauma for Assessment of Injury in Military Settings: A Meta-analysis" Balkan Med J. Dec. 20, 2019;37(1):3-8. Epub Oct. 9, 2019., in 6 pages.
Quinn et al., "What is the utility of the Focused Assessment with Sonography in Trauma (FAST) exam in penetrating torso trauma?" Injury. May 2011;42(5):482-7, in 6 pages.
Redmon et al., "Yolov3: An incremental improvement" University of Washington, 2018, in 6 pages.
Redmon et al., "YOLO9000: Better, Faster, Stronger" Proceedings of the IEEE Conference on Computer Vision and Pattern Recognition (CVPR), 2017, pp. 6517-6525, in 9 pages.
Savell et al., "Military Use of Point of Care Ultrasound (POCUS)" J Spec Oper Med. 2021 Summer;21(2):35-42, in 16 pages.
Stengel et al., "Point-of-care ultrasonography for diagnosing thoracoabdominal injuries in patients with blunt trauma" Cochrane Database Syst Rev. Dec. 12, 2018;12(12), in 129 pages.
Tan et al., "Comparison of RetinaNet, SSD, and YOLO v3 for real-time pill identification" BMC Med Informatics Decision Making. Nov. 22, 2021;21(1):324, in 11 pages.
Van der Weide et al., "Prehospital ultrasound in the management of trauma patients: Systematic review of the literature" Injury. Dec. 2019;50(12):2167-2175. Epub Sep. 28, 2019, in 9 pages.
Van Sloun et al., "Deep Learning in Ultrasound Imaging" Proc IEEE 2020;108(1), in 19 pages.
Ward, 2023. "Pre-hospital ultrasound: a review of its applications and effectiveness" Journal of EMS Medicine, 2023, in 6 pages.
Wehbe et al., "Validating Deep Learning to Distinguish Takotsubo Syndrome From Acute Myocardial Infarction—Beware of Shortcuts, Human Supervision Required" JAMA Cardiology. May 1, 2022;7(5):477-479, in 3 pages.
Wilson et al., "Validation and Clinical Applicability of Whole-Volume Automated Segmentation of Optical Coherence Tomogra-

(56) References Cited

OTHER PUBLICATIONS phy in Retinal Disease Using Deep Learning" JAMA Ophthalmology. Sep. 1, 2021;139(9):964-973. in 10 pages.
Wu, et al., 2022. "Development and validation of an end-to-end deep learning pipeline to measure pericardial effusion in echocardiography" Frontiers in Cardiovascular Medicine, in 10 pages.
Potter et al., J.A., 2023. "Automated detection and localization of pericardial effusion from point-of-care cardiac ultrasound examination" Medical & Biological Engineering & Computing, in 13 pages.

* cited by examiner

Prediction

Ground-truth (b)

(a)

AUTOMATED AND RAPID DETECTION AND LOCALIZATION OF FREE FLUID ON FOCUSED ASSESSMENT WITH SONOGRAPHY IN TRAUMA (FAST) EXAMINATION USING DEEP LEARNING

CROSS-REFERENCE TO RELATED APPLICATIONS

This application claims priority to U.S. Prov. App. No. 63/476,538 titled "AUTOMATED AND RAPID DETECTION AND LOCALIZATION OF HEMOPERITONEUM ON FOCUSED ASSESSMENT WITH SONOGRAPHY IN TRAUMA (FAST) EXAMINATION USING DEEP LEARNING" and filed on Dec. 21, 2022, the disclosure of which is hereby incorporated herein by reference in its entirety.

GOVERNMENT LICENSE RIGHTS

This invention was made with government support under Grant No. 2R44GM123821 awarded by the National Institute of Health. The government has certain rights in the invention.

BACKGROUND

Technical Field

The present disclosure relates generally to medical analysis. Specifically, the present disclosure relates to enhanced medical analysis using machine learning techniques.

Description of Related Art

The use of point-of-care ultrasonography (POCUS) has gained wide acceptance in diverse practice settings including in the emergency department, prehospital, military and austere settings because of the capability of this technology to rapidly and accurately and noninvasively rule-in serious injury by detecting free intra-abdominal, intra-thoracic and intra-pericardial fluid (blood in case of trauma). The FAST exam has become standard of care for the evaluation of patients with trauma and has been accepted as a part of the American Trauma Life Support (ATLS) protocol in the United States. The use of the FAST exam in trauma centers has been shown to decrease the time to operative management, shorten the length of stay in the hospital, and lower patient costs.

However, the FAST exam interpretation requires substantial training and can have differences in interpreter accuracy, with sensitivity and specificity of the FAST exam ranging between, as an example, 87-98% and specificities ranging between, as an example, 99%-100% in detecting intraperitoneal fluid in patients who suffer from blunt trauma. The primary limitation to the generalized use of the FAST exam has been the lack of trained and experienced operators in all types of clinical settings, including pre-hospital (e.g. emergency transport, mass-casualty, battlefield medicine) and resource-limited settings.

Teleultrasound is a proposed solution and refers to instruction provided virtually by a trainer. It has been shown to be feasible and non-inferior to in-person instruction for image acquisition and interpretation. However, this still requires a trainer or expert to be available in real-time to provide this feedback.

SUMMARY

The disclosed technology may be embodied in a computer-implemented method, system, and computer storage media. The method includes obtaining medical images associated with a patient, the medical images being ultrasound images depicting different portions of the patient, and the ultrasound images forming video of the different portions; providing the medical images to a machine learning model, wherein a forward pass through the machine learning model is computed, and wherein the machine learning model is trained to output for each input medical image, a bounding box about free fluid depicted in the input medical image and a confidence score associated with detection of the free fluid in the bounding box; and determining that the patient has free fluid based on analyzing output from the machine learning model.

Figure 1A:
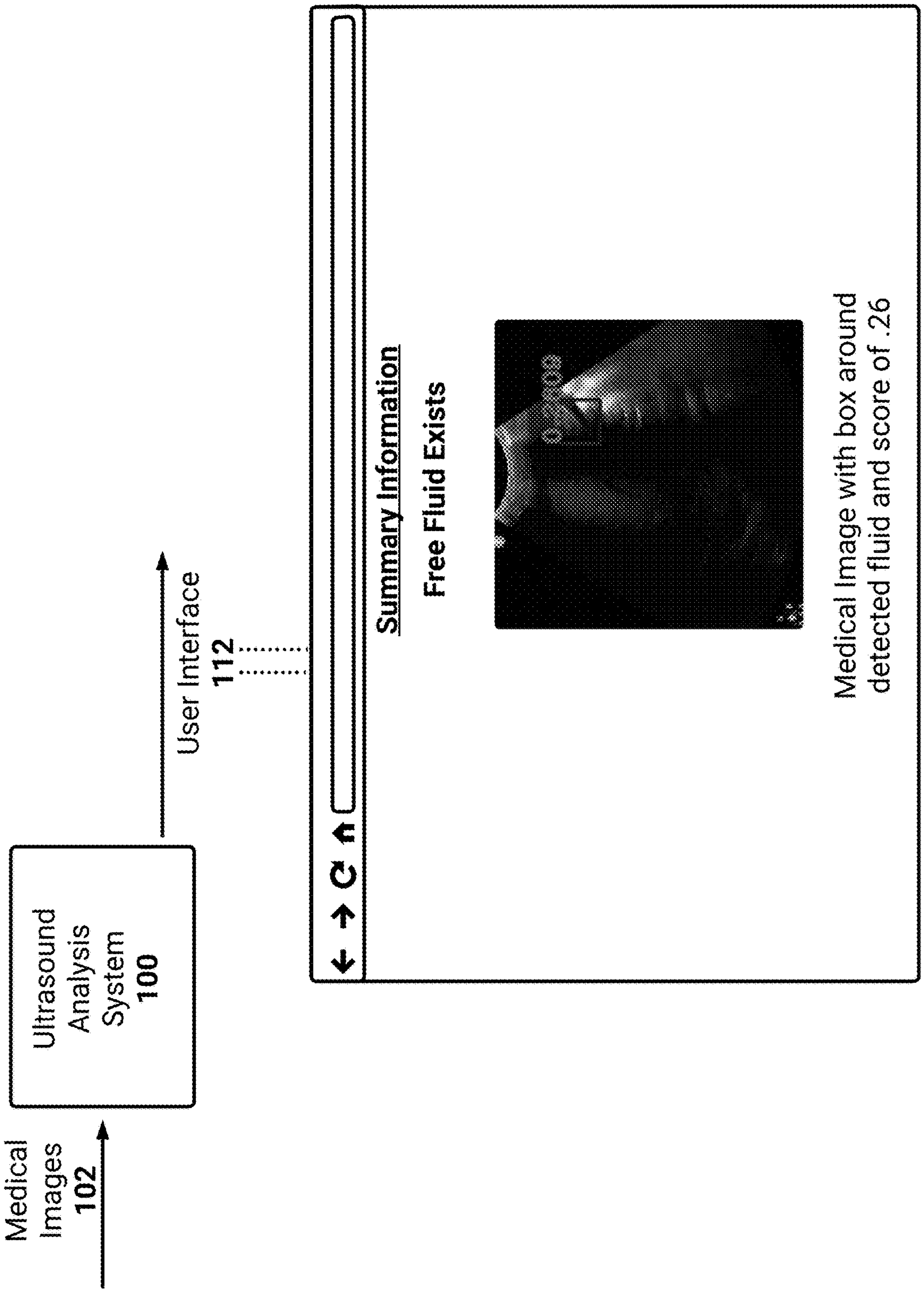
FIG. 1A illustrates a block diagram of an example ultrasound analysis system presenting a user interface based on input of ultrasound images or video frames.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

This application describes techniques to rapidly, and accurately, identify the presence and location of free fluid in focused assessment with sonography in trauma (hereinafter FAST) exams of patients with free fluid. In some embodiments, a machine learning model may be used. An example machine learning model may include a deep learning model, such as a convolutional neural network, attention-based network, dense (e.g., fully-connected network), and so on. In some embodiments, ultrasound images or video frames may be input into the machine learning model and output information (e.g., free fluid locations, corresponding confidence scores, and so on) obtained. The output information may be used, for example by medical professionals, as a real-time aide to identify patients who have a positive FAST from free fluid.

As will be described, a system described herein (e.g., the ultrasound analysis system 100) may receive a multitude of ultrasound images or video frames. The system may then compute a forward pass through a machine learning model to detect and localize free fluid in the images or video frames.

If there are multiple detections in one image or video frame, the system may maintain the detection with the highest confidence. In some embodiments, the system may be designed to correctly classify each case (e.g., patient case) as a binary result of positive vs. negative. Thus, maintaining the highest confidence may sufficient information for free fluid detection with high prediction performance. Having recorded the resulting detections and confidence scores for each frame of each ultrasound case, the system may represent each case with the highest confidence score across all frames. The system may additionally threshold the confidence score to classify the case as positive or negative. In some embodiments, the classification may be non-binary. For example, there may be 3, 4, 5, 6, and so on, classifications. In some embodiments, a user of the system may create custom classifications each with a range of confidence scores.

As an example, the machine learning model may receive an image or video frame. For this example, the system may obtain a detected object. The detected object may include free fluid. The system may additionally obtain a confidence score associated with the detection. Advantageously, in some embodiments the machine learning model may output the detected object and confidence score based on the same forward pass. For example, the machine learning model may include YoloV3, and so on. The system may then use the cumulative scores in each video to classify the video.

To ensure accuracy, in some embodiments the machine learning model may be trained, validated, tested, and so on, using only, or substantially only, cases of free fluid. For example, in some embodiments training data in which free fluid caused by ascites, dialysis fluid, congestive heart failure, and so on, are not used.

In contrast to the machine learning techniques described herein, another technique may include using classification techniques which leverage residual networks. For example, the residual networks may receive a video frame and predict to which category the frame belongs (e.g., the FAST exam view). This classification technique has technical deficiencies. For example, through doing classification at the outset, rather than based on analyzing confidence scores as described herein, these techniques fail to unravel the location of free fluid after classification.

An additional technique may include a machine learning model which performs pixel-by-pixel segmentation of free fluid. However, the performance (e.g., accuracy) of this additional technique is lower than through use of the techniques described herein. As may be appreciated, classification using a pixel-by-pixel approach is substantially more computationally expensive. For example, the techniques described herein may be substantially faster in inference time thus enabling more feasibility for point-of-care applications.

The techniques described herein address technical problems through use of efficient machine learning models which are specifically trained to provide substantial accuracy. Through use of these machine learning models, for example to analyze the FAST exam, the system described herein can identify both the presence and location of free fluid in substantially real-time. Providing the location of free fluid identified by the application allows a medical professional (e.g., a clinician) to visualize and overread the interpretation, similarly to the functionality of an automated electrocardiogram interpretation provided on each report. Moreover, as FAST exam is used in emergency care settings, high accuracy in free fluid detection should be paired with the capability of rapid inference.

The proposed technology represents a significant improvement over the state-of-the-art approaches by increasing access to point-of-care ultrasonography (POCUS), which include a broader application of POCUS training and/or telemedicine. Ultrasound image transfer for off-site interpretation has been shown to be feasible. However, this requires not only a reliable data connection but also an on-site technician who is trained to acquire images correctly. While robotic tele-manipulation of an ultrasound probe by an off-site expert sonographer has also been explored, inherently decreases portability and may be difficult to use in the setting of trauma. An alternate approach is to broaden FAST training to include paramedics and non-physician personnel in rural emergency departments and urgent care settings (such as nurse practitioners and physician assistants). However, substantial cost and time burdens related to training make this prohibitive.

Even with a broader application of POCUS training an automated system, such as described herein, provide a valuable secondary assessment. The system described herein represents an innovative, and first, implementation of machine learning techniques which can rapidly indicate the location of accurate positive findings to aid both untrained operators as well as trained clinicians in their interpretation.

Automated tools that aid clinical workflow are being tested for adoption at large clinical institutions. Thus, in addition to resource-constrained settings (e.g., rural and community hospitals, lower to middle-income countries, and pre-hospital settings) discussed above, the system described herein can impact high-volume trauma centers and large institutions to increase operational efficiency. Moreover, the system can be used in non-emergent settings, for example, by in-patient or out-patient internists looking for ascites or pericardial effusions. Much like the automated electrocardiogram read, automated abdominal or pericardial free fluid detection could assist a wide variety of providers in ultrasound interpretations to detect free fluid. In the longer term, the techniques described herein can be expanded for automatic analysis of medical images that are taken every day in hospitals and clinics to aid experts in screening for various diseases and conditions. The rapid inference capability will enable detection of diseases and conditions at early stages, thus facilitating preventive measures and better care.

The above will now be described in more detail.

FIG. 1 is a block diagram of an example ultrasound analysis system 100 generating a user interface 112. The ultrasound analysis system 100 may represent a system of one or more processors, such as a user device, a computer, a back-end server system, and so on. As described above, the system 100 may receive medical images 102 for analysis. The system 100 may additionally present a user interface 112 for interaction with by an end-user (e.g., a medical professional). The system 100 may, in some embodiments, present the user interface 112 via a display of the system. The system 100 may also cause presentation of the user interface 112 via a display of a different system or user device (e.g., the user interface 112 may represent a front-end of a web application).

In the illustrated example, the ultrasound analysis system 100 has received medical images 102 associated with a patient. The medical images, as described above, may represent ultrasound images or video frames. The system 100 may utilize example machine learning techniques to determine whether free fluid (e.g., bleeding, such as intra-abdominal bleeding) exists. As described herein, the techniques may thus efficiently perform the FAST exam. The medical images may depict portions of the patient's body, for example as known by those skilled in the art the images may depict the pericardium and spaces within the peritoneal cavity. For example, the spaces may include the right upper quadrant (RUQ), the left upper quadrant (LUQ), and so on. The medical images may additionally depict the heart (e.g., cardiac images).

The system 100, as will be described, may determine locations (e.g., bounding boxes) about free fluid depicted in the medical images 102. In some embodiments, the system 100 may additionally determine confidence values associated with the existence of free fluid. Based on the output confidence values, the system 100 may determine the existence of free fluid. In FIG. 1, the system 100 has updated user interface 112 to include summary information associated with its analysis. For example, the summary information may include the analyzed medical images 102 with bounding boxes, confidence scores, and so on. The summary information may additionally include a medical image with a highest confidence score. Textual descriptions related to the medical images may be included. For example, the system 100 may identify a location within the patient of the free fluid (e.g., RUQ, LUQ, the heart, and so on).

Figure 1B:
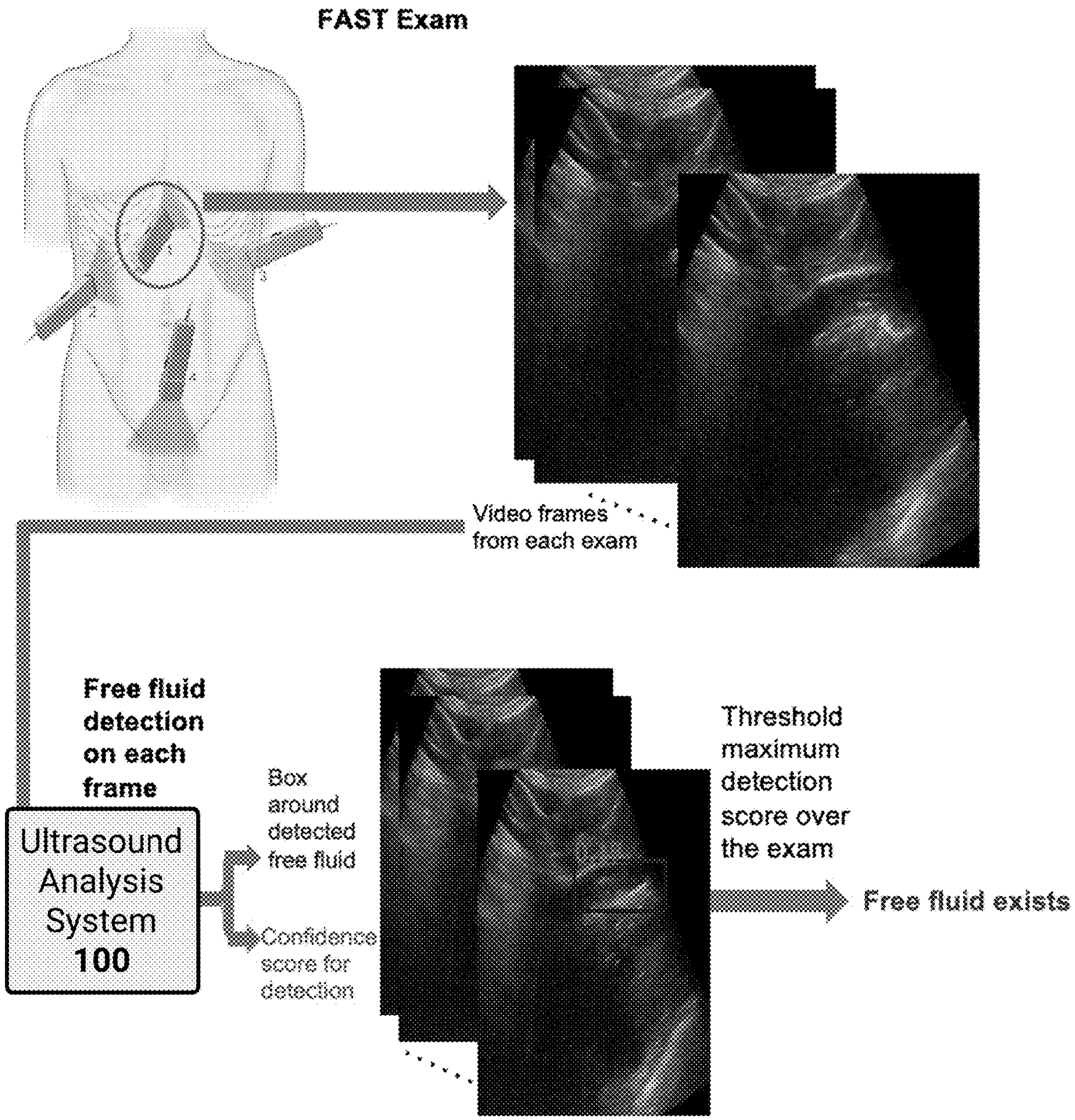
FIG. 1B is a graphical depiction of performance of the FAST exam using the ultrasound analysis system.

FIG. 1B is a graphical depiction of performance of the FAST exam using the ultrasound analysis system 100. In the illustrated example, medical images from different portions of a patient's body are obtained. The medical images, such as video frames from each exam (e.g., exams 1-4), may be provided to the ultrasound analysis system 100 described above. The system 100 may determine whether free fluid exists in accordance with a FAST exam.

The ultrasound analysis system 100 may be trained to perform the FAST exam as described herein. In some embodiments, deidentified FAST exam video clips may be used for training a machine learning model. For videos that belong to positive cases, in some embodiments segmented regions in each frame may be identified which indicate a visible area of free fluid. Each image may optionally be coded by a threshold number of reviewers (e.g., 1, 2, 3 human or software-based reviewers) to reach consensus on all areas on a unique image where free fluid was detected. Each image may therefore be coded independently of other images because free fluid may not be seen in each image of a FAST exam due to the operator scanning through the entire area of interest in the body.

To prepare the above-described ground-truth labels for the free fluid detection algorithm, the free fluid regions in the training data may be mapped to bounding boxes. For each quadrant (e.g., portion of the patient), the resulting dataset may be partitioned into training, validation, test cases. For example, the portioning may be via 5-fold cross validation in a stratified manner, keeping a uniform ratio of positive and negative cases in each set.

As described above, the machine learning model may represent a convolutional neural network which is trained to analyze the ultrasound images described herein. In some embodiments, the model may represent an attention-based vision network. In some embodiments, the you only look once (YOLO, or YOLOV3) model may be used to automatically detect free fluid. As known by those skilled in the art, YoloV3 is a real-time object detection algorithm capable of identifying specific objects in images, using latent features learned by a deep convolutional neural network to detect an object. Unlike classifier-based object detection approaches that perform inference on multiple candidate locations and scales to find high confidence detections, the YoloV3 algorithm employs the same convolutional network on image region partitions and predicts bounding boxes and probabilities for each region, significantly accelerating inference compared to former methods. These bounding boxes are weighted by the predicted probabilities to form the final detections. The system 100 may therefore leverage the model, such as YoloV3, to receive a 2D video frame and makes two sets of predictions: (1) rectangular bounding boxes that circumscribe potential free fluid regions, and (2) the confidence score in the range [0,1] that is associated with each free fluid detection. Thus, as may be appreciated YoloV3 includes a multitude of sequential convolutional layers, one or more dense (e.g., fully-connected layers) to output predictions, and so on.

Using the trained machine learning model, the system 100 may perform post-processing steps to determine free fluid presence for each exam using the detection with the highest confidence score across all the medical images. For example, the highest confidence score may be compared with a threshold. Using the highest confidence score across all images for final diagnosis considers the fact that all images in the video are correlated. In doing so, the system reduces the effect of detected boxes that may be false negatives or positives for specific still images, as they typically attained lower confidence scores. In some embodiments, the medical images from different locations or positions may be associated with different threshold confidence scores to be considered as having free fluid. Thus, RUQ, LUQ, the heart, and so on, may have different threshold confidence scores.

Due to the difficulty of obtaining training data, in some embodiments transfer learning may be employed by initializing the weights of the neural network with weights pretrained on a benchmark object detection dataset. An example dataset includes the Common Objects in Context dataset. Following initialization, the system may train the machine learning model on pairs of video frames and corresponding ground-truth free fluid boxes that belong to positive training cases.

In some embodiments during training, and in an effort to better generalize the performance over unseen cases, input frames may be perturbed via Gaussian distributed additive noise. To apply Gaussian noise, the system 100 may sample a value from a Gaussian distribution with 0 mean independently for each pixel of each training image and added the sampled value to the pixel value.

The system 100, as described above, may apply the trained model on each video frame in the test set to detect free fluid boxes and corresponding confidence scores. If there are multiple detections in one frame, the system may maintain the detection with the highest confidence. Having recorded the resulting detections and confidence scores for each case, the system 100 represents each case with the highest confidence score across all frames and thresholds the score to classify the case as positive or negative. In embodiments in which negative cases are not used for training, this technique may lead to the least false positive detections on the negative validation and test cases.

In some embodiments, to aid neural network training, pixel values may be normalized between 0-1. To do so, the maximum pixel value in each video may be computed and each pixel value within the video was divided by this value. This process also aimed to mitigate the common lighting and contrast variations across different ultrasound videos.

The system 100 may tune the threshold for positive vs. negative classification to attain similar specificity and sensitivity over the validation set cases. Then, the system 100 may apply the machine learning model on the test set to obtain the highest confidence score per case and threshold each score at the best validation threshold to classify the case as positive or negative.

Figure 2:
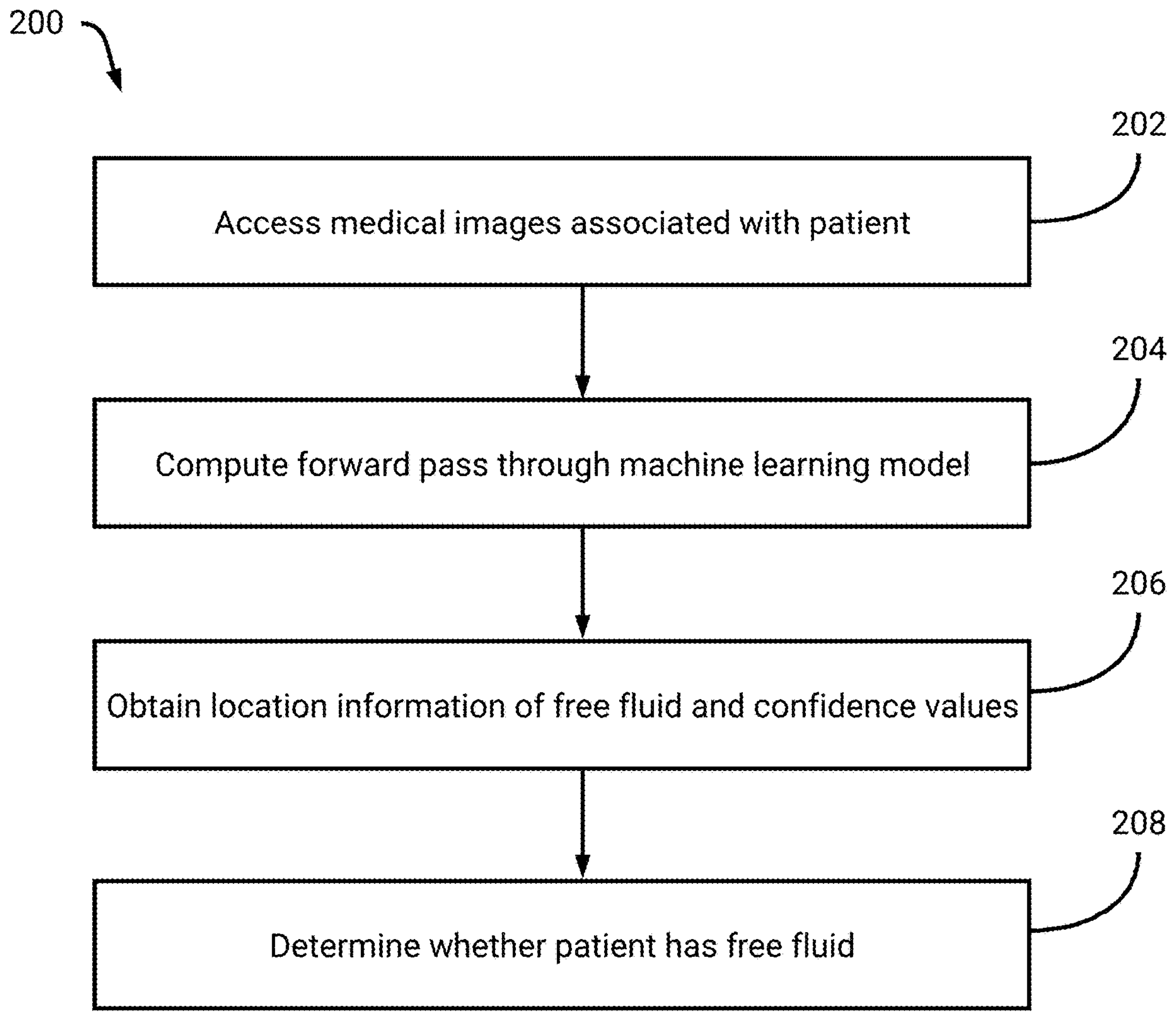
FIG. 2 is a flowchart of an example process to perform the FAST exam using machine learning techniques.
Figure 3:
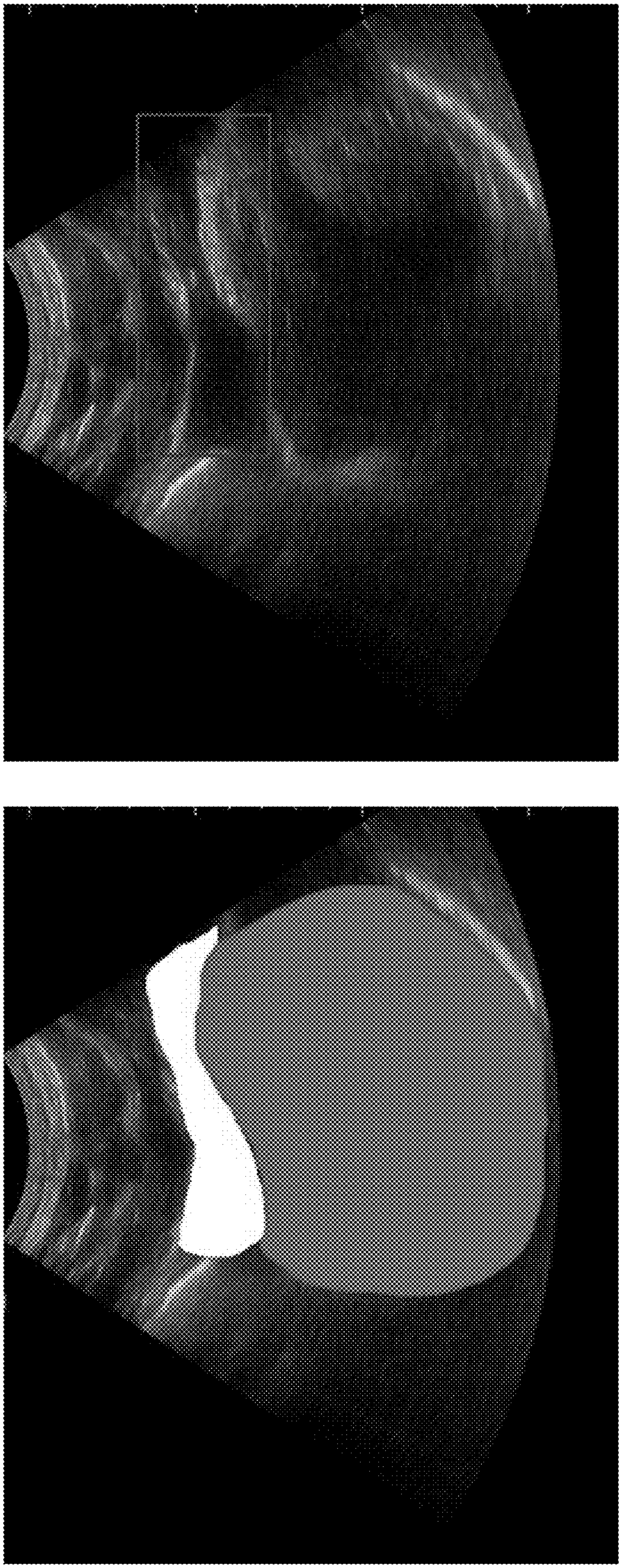
FIGS. 3-16 illustrate example user interface outputs.
Figure 4:
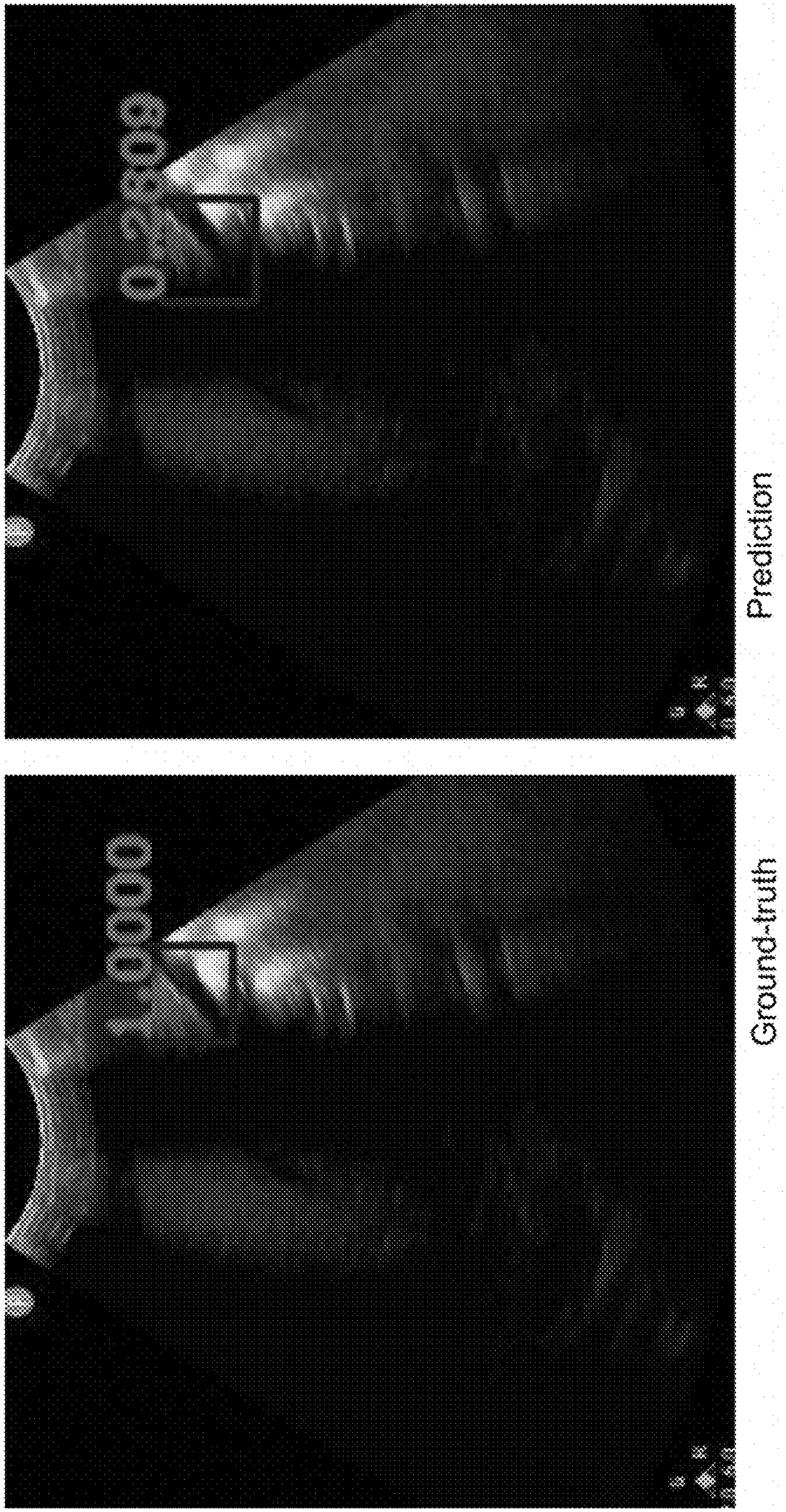
Figure 5:
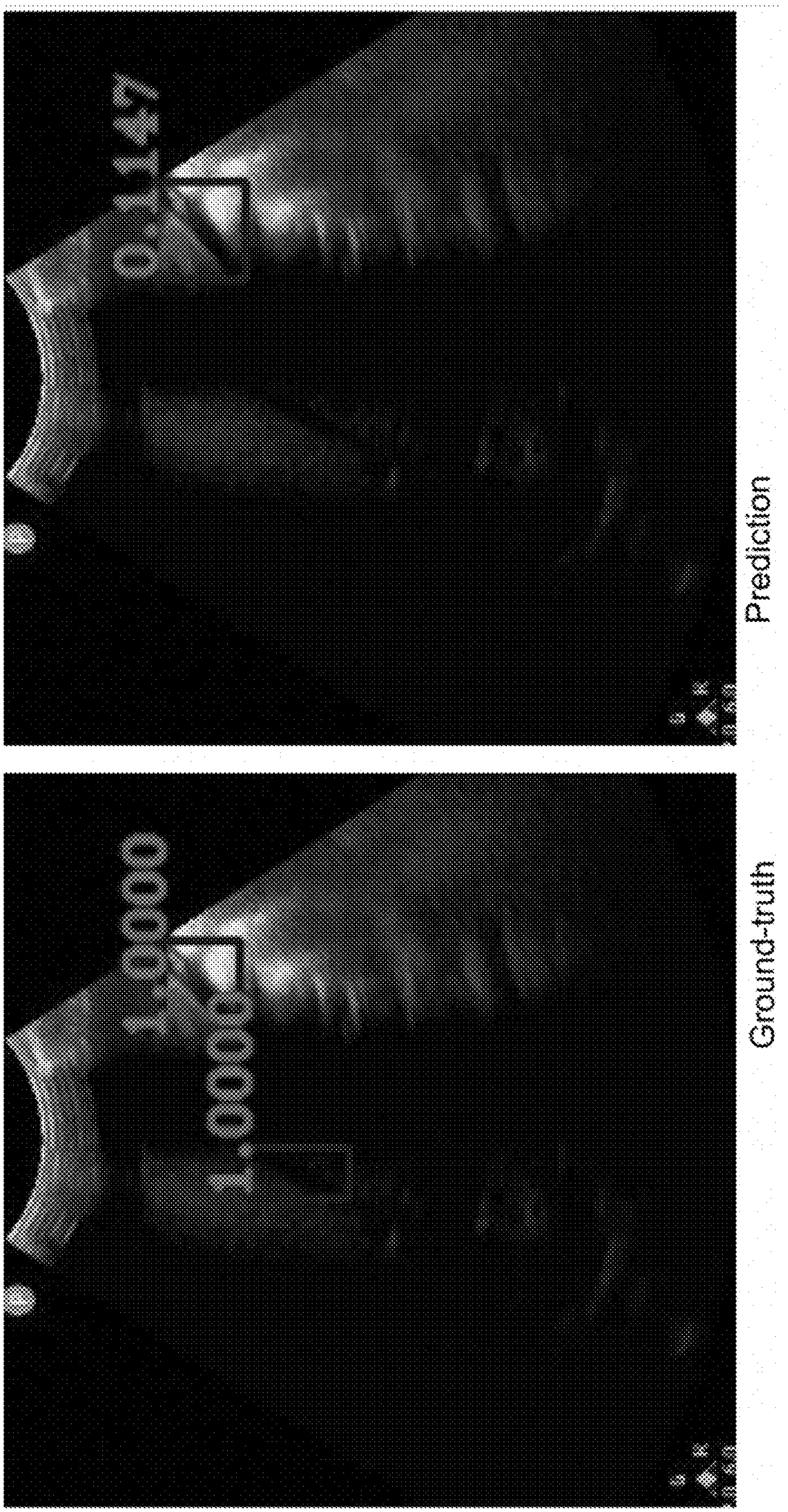
Figure 6:
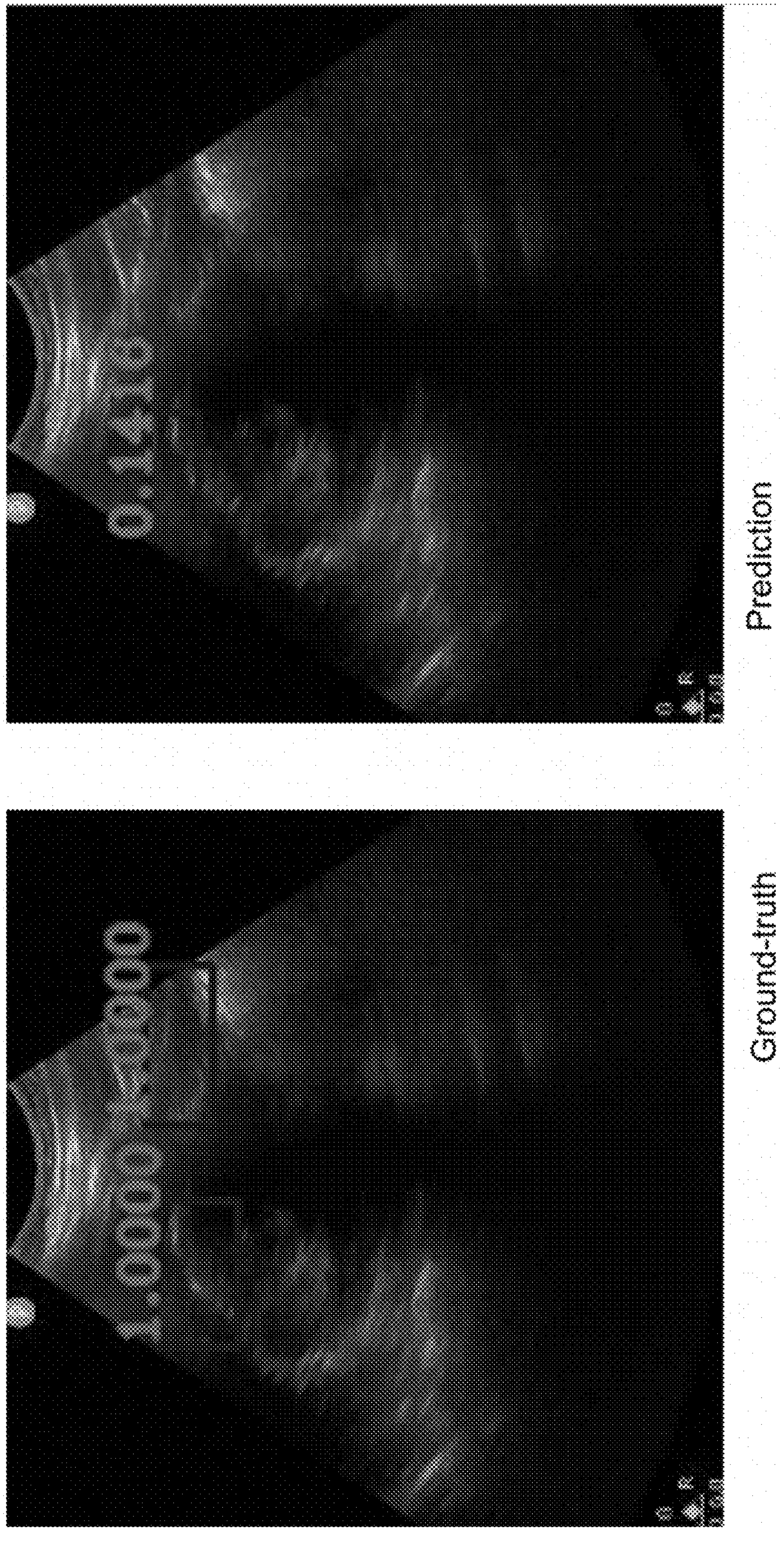
Figure 7:
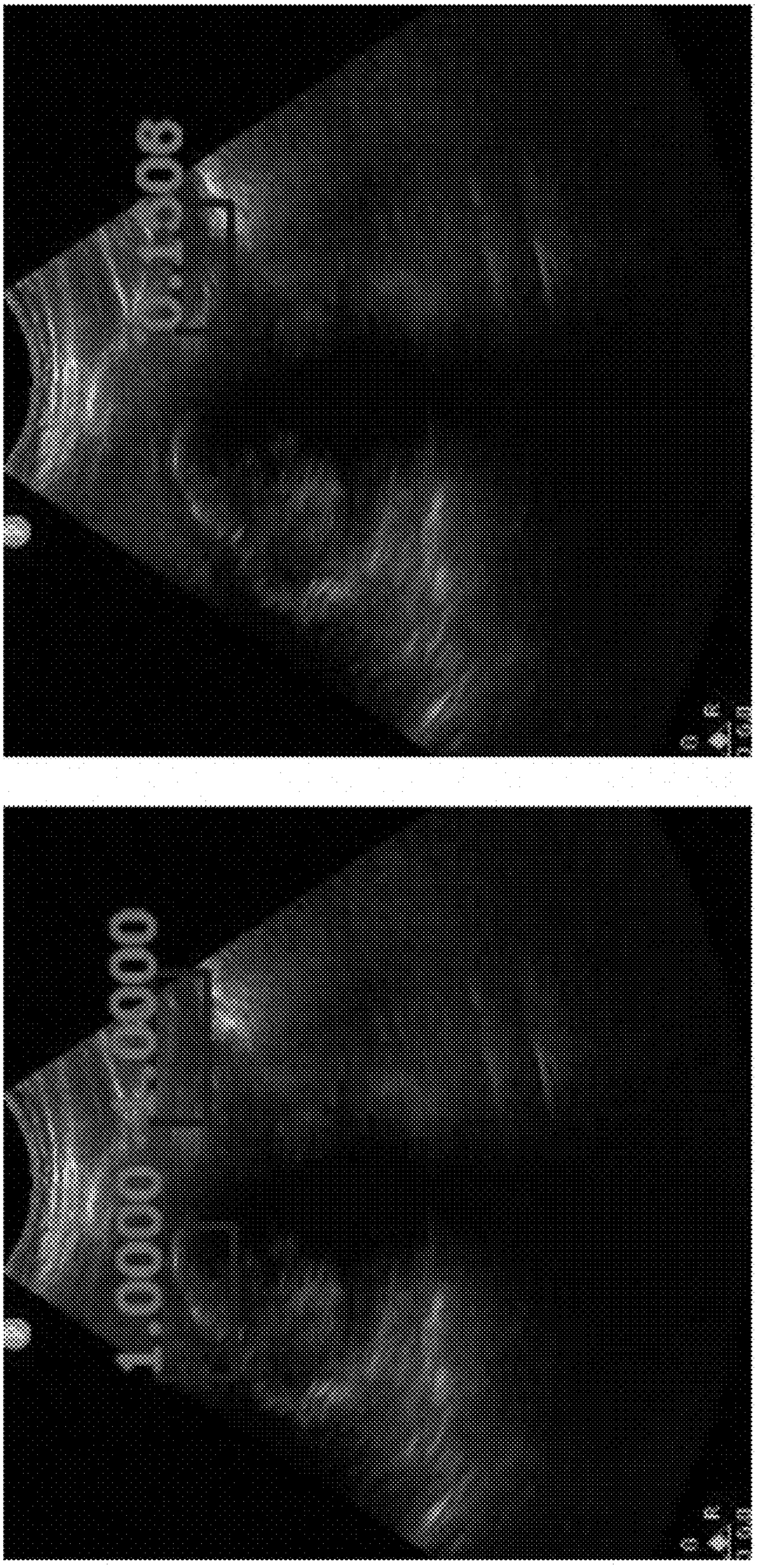
Figure 8:
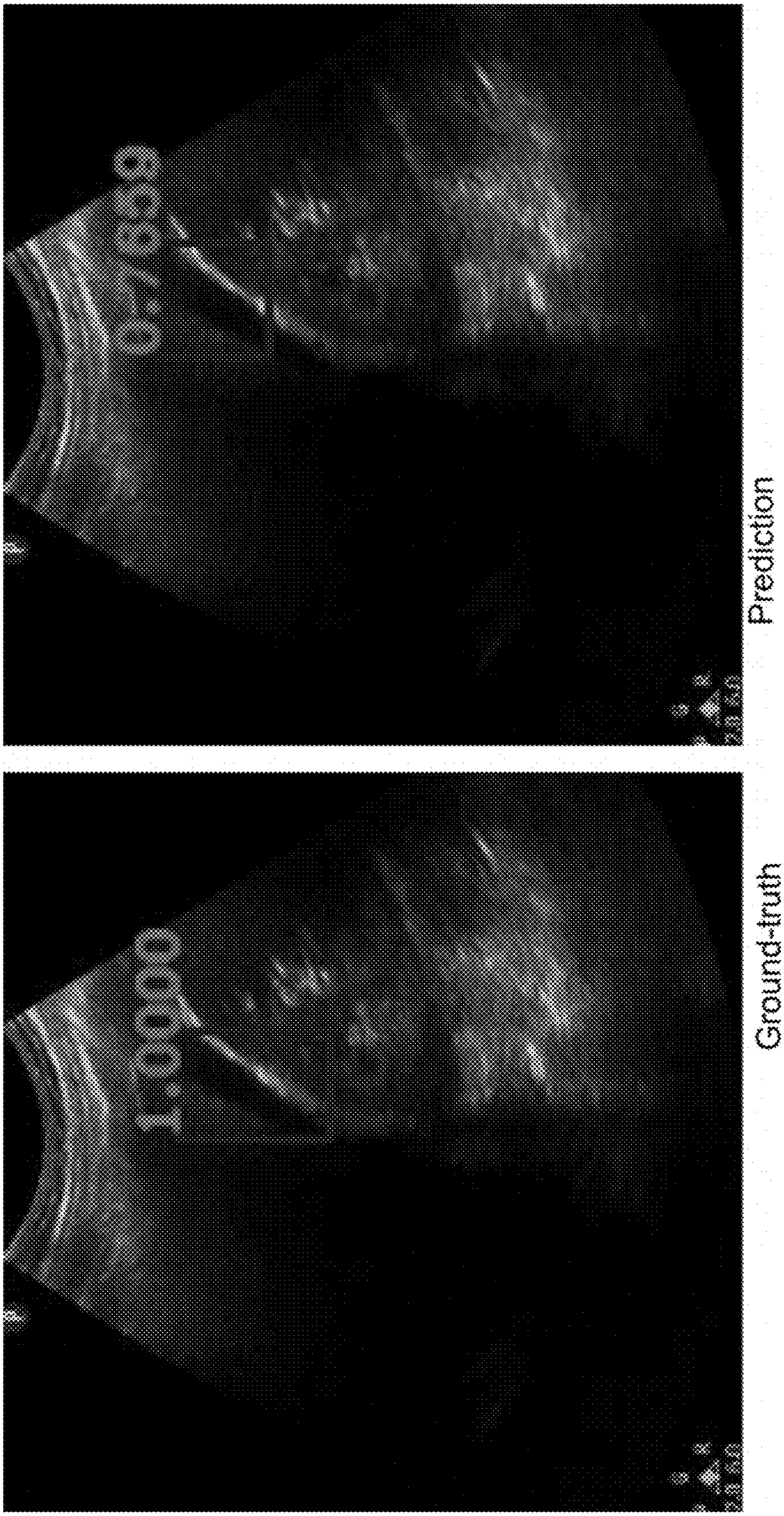
Figure 9:
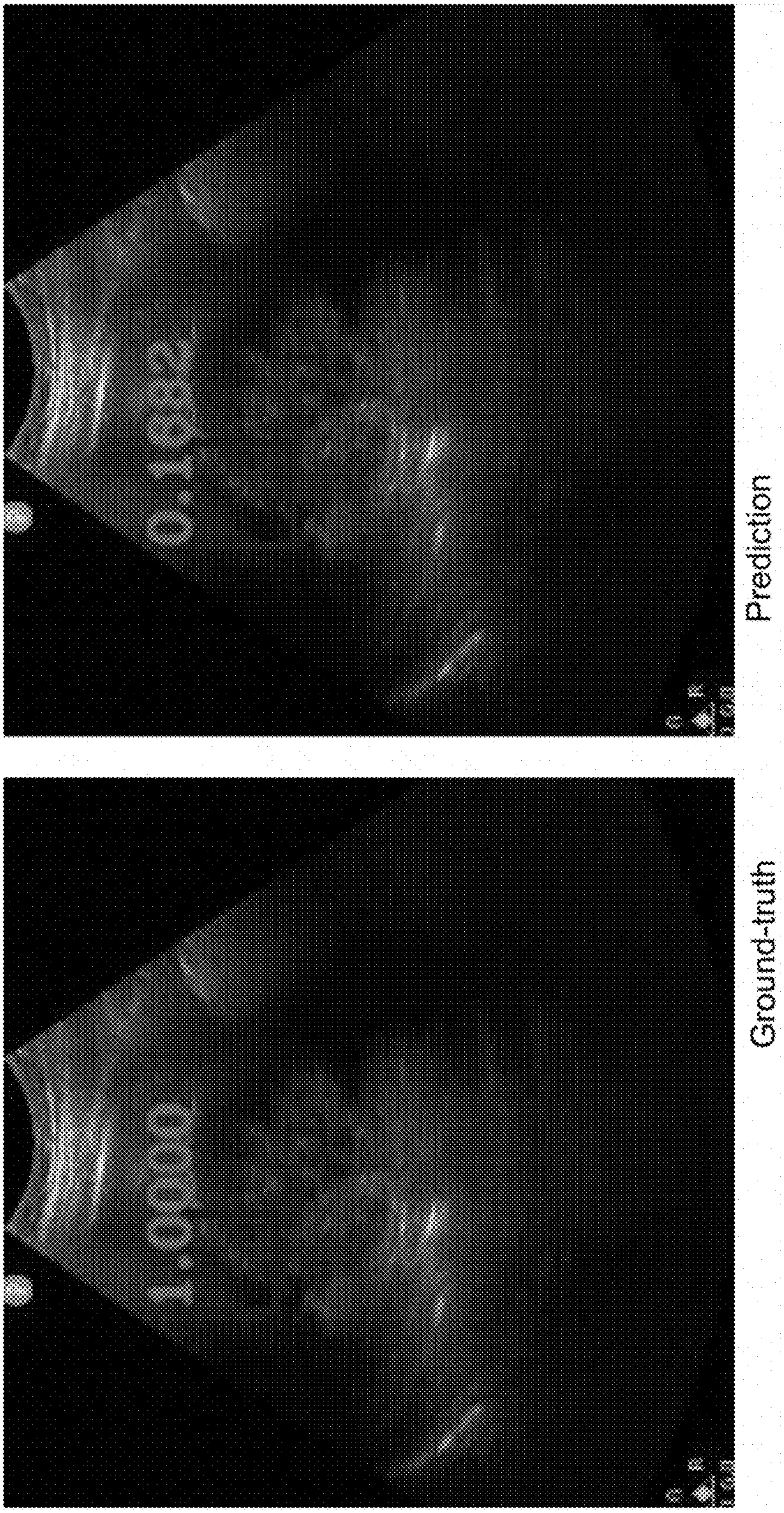
Figure 10:
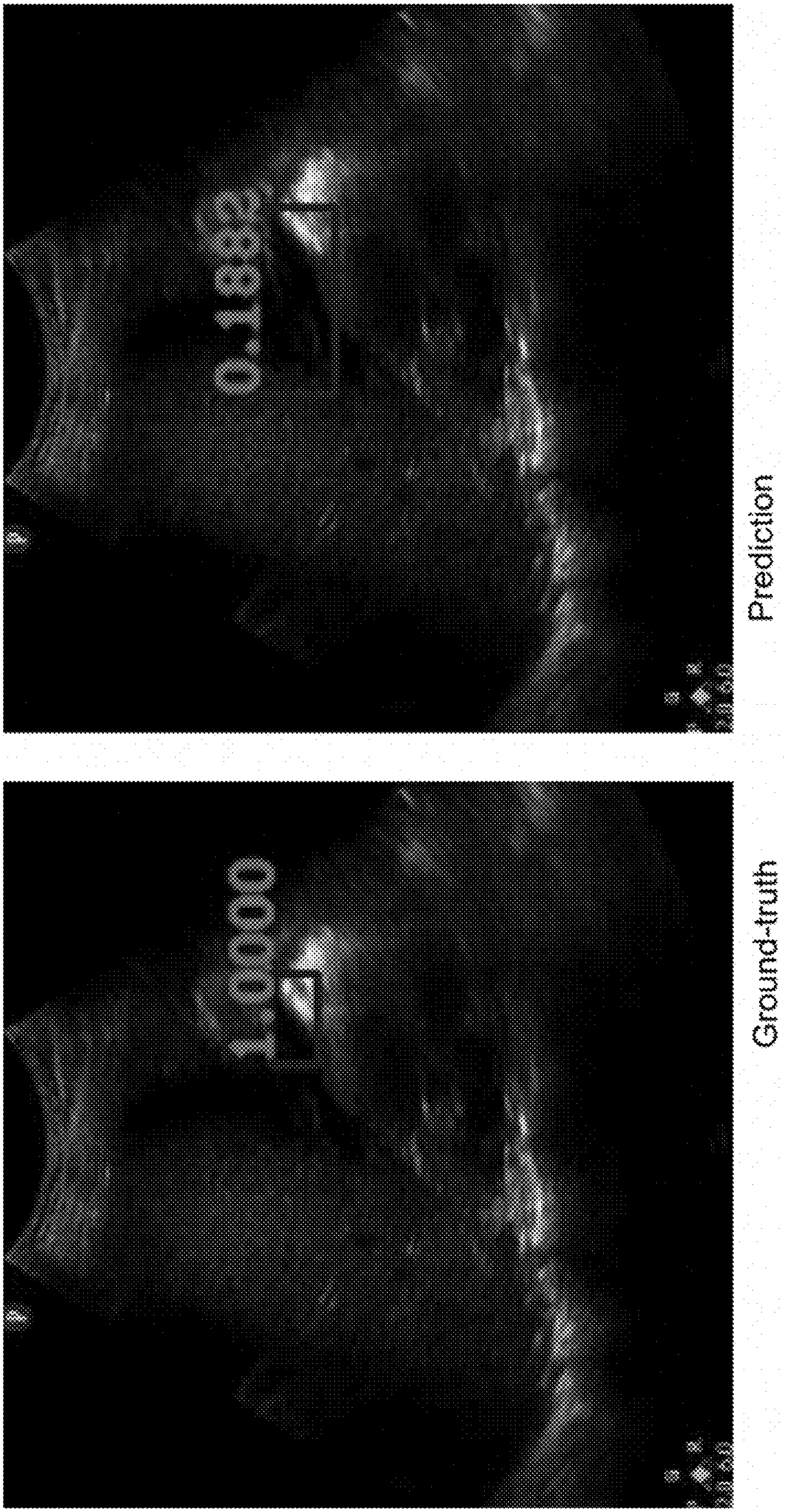
Figure 11:
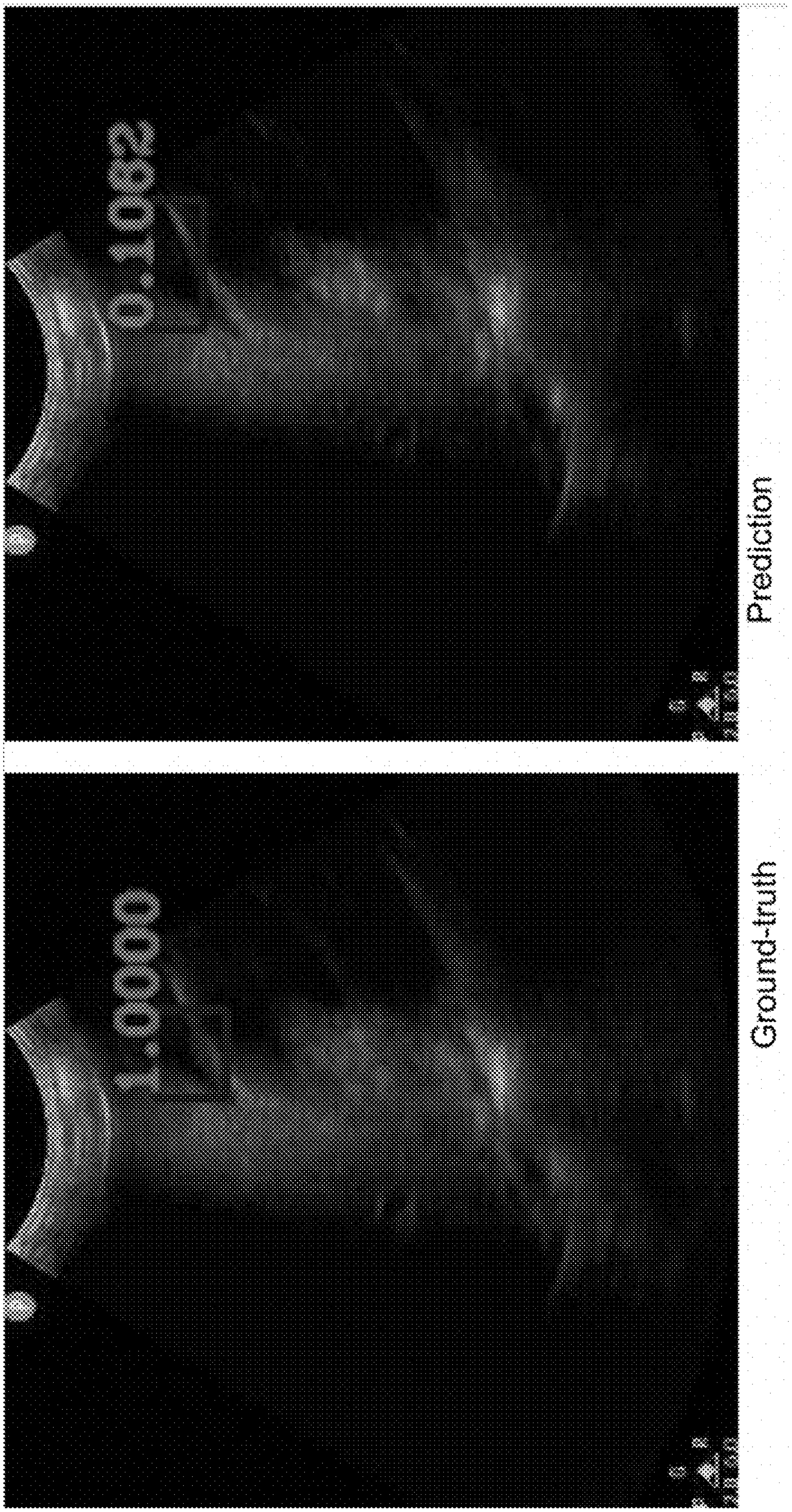
Figure 12:
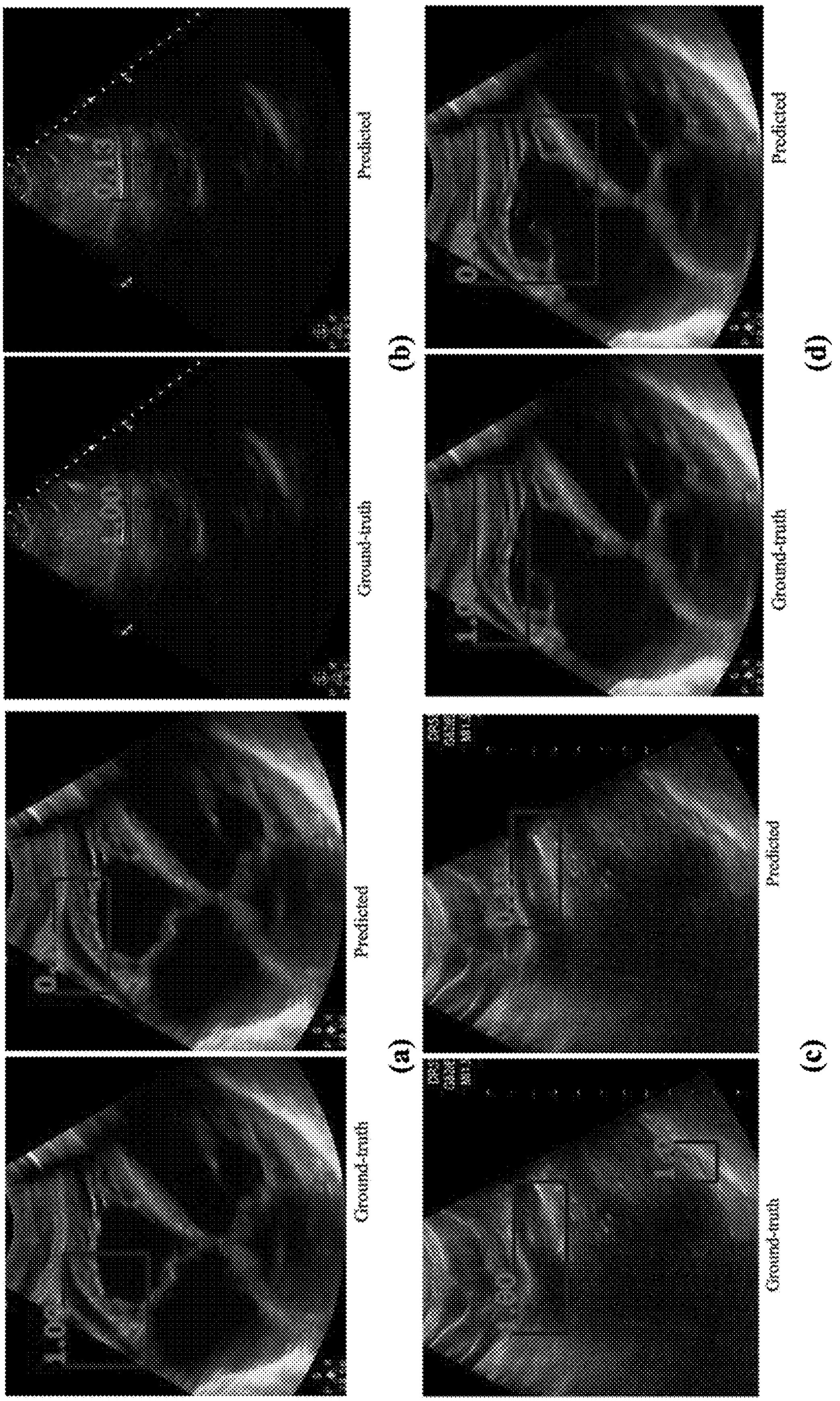

FIG. 2 is a flowchart of an example process to perform the FAST exam using machine learning techniques. For convenience, the process 200 will be described as being performed by a system of one or more computers (e.g., the ultrasound analysis system 100).

At block 202, the system accesses medical images associated with a patient. As described above, the medical images may represent ultrasound images or video frames. The medical images may depict different portions of the patient. For example, a medical professional or automated system may cause an ultrasound probe to obtain the medical images from a particular or set of positions on the patient.

At block 204, the system computes a forward pass of the medical images through a machine learning model. As described above, the machine learning model may represent a neural network (e.g., a convolutional neural network)

At block 206, the system obtains individual location information (e.g., a bounding box) of free fluid and individual confidence scores for the medical images.

At block 208, the system determines whether the patient has free fluid in accordance with a FAST exam. The system may determine that the patient has free fluid, for example in a particular portion of the patient, based on a confidence score exceeding a threshold (e.g., 0.3, 0.4, 0.5, 0.98).

Example Results

Table 1 shows example performance of the techniques described herein on distinguishing positive and negative cases for each quadrant. All classification metrics attained 90% or above on average over considered quadrants, following the typical rule-of-thumb of diagnostic testing and demonstrating the discrimination capability of the confidence scores of detected boxes.

Along with classification, free fluid was localized on the video frames of positive cases due to employing the machine learning model. The intersection over union (IOU) metric computed over the positive cases was affected by both localization performance, as well as the sizes and aspect ratios of the detected boxes. As demonstrated below, the technique described herein algorithm exhibited strength in good localization, while the detected box sizes and aspect ratios varied and affected the average IOU.

TABLE 1

Classification and localization performance of free fluid detection

| Quadrant | Specificity | Sensitivity | Accuracy | AUC | IOU |
|---|---|---|---|---|---|
| RUQ | 0.94 (+/−0.1) | 0.95 (+/−0.1) | 0.95 (+/−0.09) | 0.97 (+/−0.08) | 0.56 |
| LUQ | 0.9 (+/−0.29) | 0.92 (+/−0.22) | 0.88 (+/−0.13) | 0.94 (+/−0.07) | 0.31 |
| Cardiac | 0.92 (+/−0.15) | 0.89 (+/−0.33) | 0.91 (+/−0.18) | 0.94 (+/−0.19) | 0.51 |

Other approaches were compared, for example approaches which the 2D U-Net, MaskRCNN, ResNet, and Single Shot Detector (SSD), and found to be deficient. The disclosed technology performs localization, for example, by drawing a box around the free fluid region to be reviewed by clinicians, rather than pixel-by-pixel exact segmentation. As a result, while the general location and region of interest of detected boxes were correct compared to the ground-truths, detected box sizes and aspect ratios varied and lowered the average IOU. The disclosed technology is designed by acknowledging this trade-off, as efficient and accurate free fluid detection is the priority in point-of-care applications, rather than the exact shape and size of free fluid.

FIGS. 3-16 provide examples of the image analysis on RUQ and Cardiac quadrants. These figures may be included in a user interface, such as user interface 112. For example, a user may view training information such as comparisons of ground truth to inference results.

Each ground-truth image displays a box around the coded free fluid region confirmed by experts. The predicted image corresponding to each ground-truth image displays a box provided by the automated algorithm that indicates the predicted free fluid region. Next to each box, a score that varies between 0 and 1 is shown, which indicates the confidence on the coded free fluid region. As expected, for expert-confirmed ground-truth boxes, confidence score is the highest value of 1.

Quantitative examples validate that the disclosed technology exhibited strength in good localization, including very small free fluid regions as in FIG. 12*b*. Naturally, confident detections corresponded to the free fluid boxes around which there is high visual contrast, as in FIG. 8. While detected locations and regions of interests were correct with respect to ground-truth boxes, detected box sizes and aspect ratios varied (e.g., FIGS. 10-11), as also discussed quantitatively above. FIGS. 5-7 and 12*c* demonstrate the cases in which there are multiple ground-truth free fluid boxes, while the disclosed technology focuses on its most confident detection per frame. As our end goal is to correctly classify each case as a binary result of positive vs. negative, this design choice provides sufficient information for free fluid detection with high prediction performance. For some Cardiac cases, detected boxes contained both the free fluid region, as well as a section of the heart, as in FIG. 12*d*. This behavior is natural, as the algorithm typically observed free fluid appearing close to the heart. Overall, when the case was correctly classified as positive with respect to the confidence score (with 89% chance as in Table 1), an expert would review the detected box in each frame and select the correctly localized free fluid region for further analysis.

Figure 13:
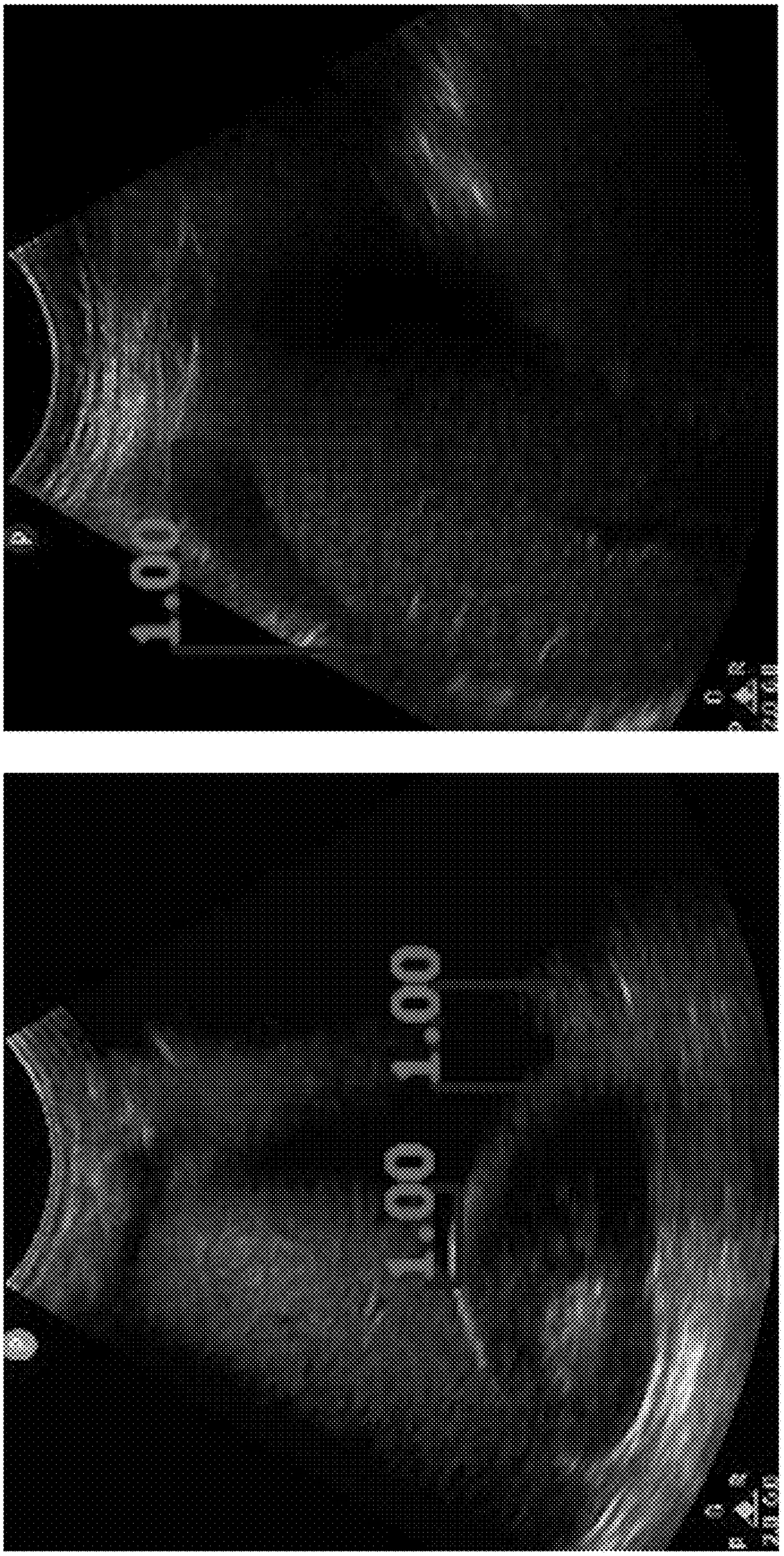
Figure 14:
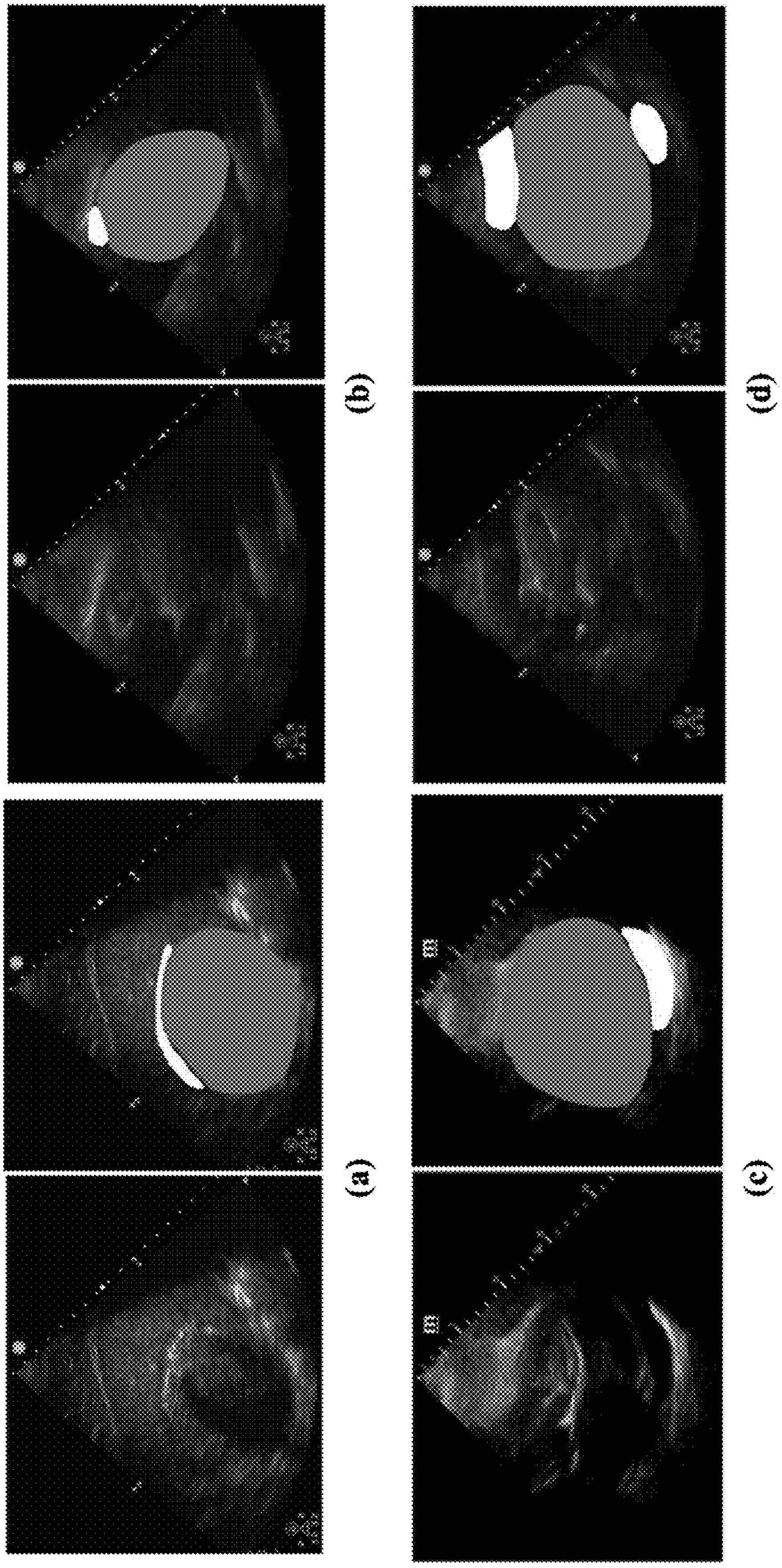

Discordant cases that were falsely labelled as negative by the disclosed technology were reviewed (FIGS. 13 and 14). RUQ cases had large areas of imaging artifacts from rib or other shadowing, which is often a pitfall for human operators and interpreters. Particularly, for the case represented in FIG. 13*a*, the larger area of free fluid was overlapped with shadows, while the higher contrast free fluid occupied a much smaller (less than 1% of the video frame) and was in a location that is harder to detect. For the case represented in FIG. 13*b*, despite the larger size of the free fluid, the contrast was lower than the typical examples shown in FIGS. 4-11. Free fluid regions in cardiac cases were not only small, but also exhibited much lower contrast compared to the heart regions. Finally, the disclosed technology could in fact detect the top pericardial effusion region in FIG. 14*d*, but with a low confidence score of 0.01 that did not pass the detection threshold.

Figure 15:
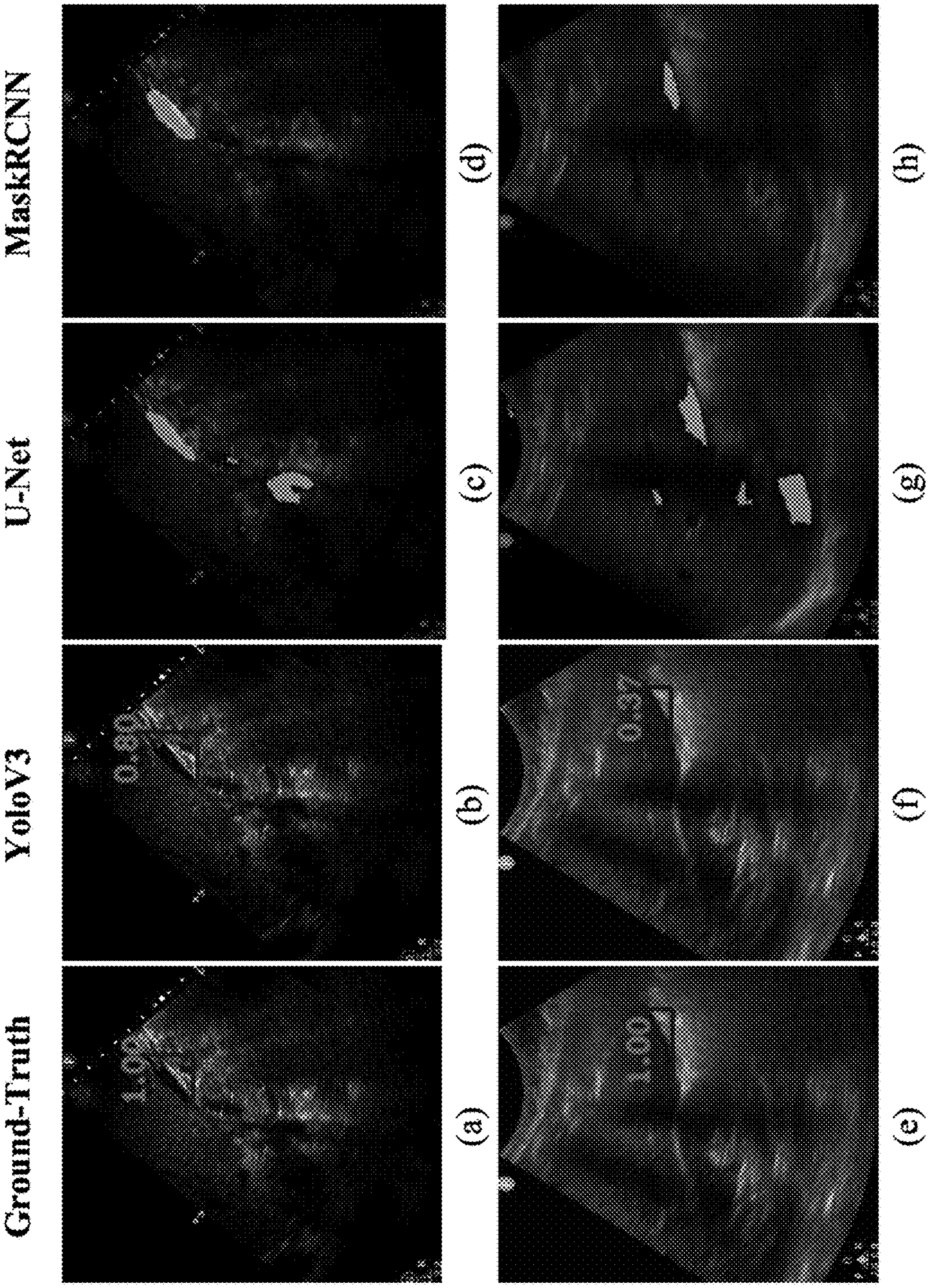
Figure 16:
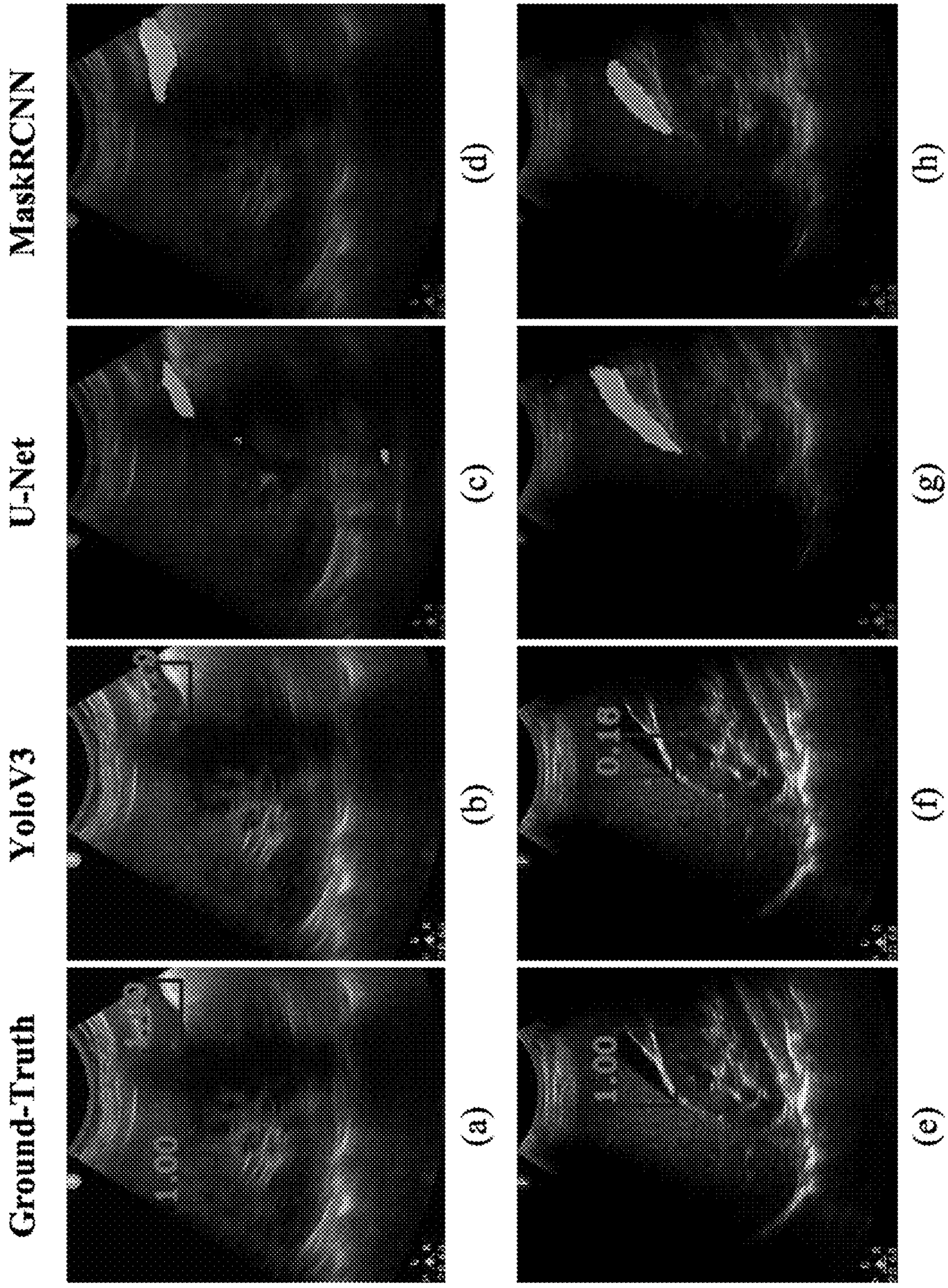

FIGS. 15-16 compare the localization performances of YoloV3 against U-Net and MaskRCNN on example frames from 4 different RUQ cases in each row and their corresponding ground-truth free fluid boxes. The case in FIG. 15 row 1 exhibits high contrast and is accordingly localized the best by YoloV3 in terms of size and shape, with 80% confidence. While the average IOU of MaskRCNN is higher than YoloV3, FIG. 15 row 2 and FIG. 16 row 1 exhibit the cases for which both YoloV3 and MaskRCNN cannot capture the exact shape and size of the ground-truth free fluid. In particular, MaskRCNN underestimates the free fluid size for FIG. 15 row 2 and includes part of the shadowing in addition to free fluid for FIG. 16 row 1. U-Net includes background regions in free fluid segmentation for most cases, including FIG. 15 and FIG. 16 row 1. FIG. 16 row 2 exhibits a case where YoloV3 considerably underestimates free fluid size compared to MaskRCNN and U-Net, while the general location and region of interest are correct compared to the ground-truth, similar to FIGS. 3-11. As also assessed quantitatively above, YoloV3 performs rapid detection and localization by drawing a box around the free fluid, rather than the less efficient pixel-by-pixel segmentation. This design choice demonstrates significantly higher accuracy in free fluid detection than all competing methods, with a trade-off in estimating the exact shape and size of free fluid around the correctly localized region of interest.

OTHER EMBODIMENTS

All of the processes described herein may be embodied in, and fully automated, via software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence or can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and engines described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

It should be emphasized that many variations and modifications may be made to the above-described embodiments, the elements of which are to be understood as being among other acceptable examples. All such modifications and variations are intended to be included herein within the scope of this disclosure.

What is claimed is:

1. A method implemented by a system of one or more processors, the system performing a focused assessment with sonography for trauma (FAST) exam, and the method comprising:

obtaining medical images associated with a patient, the medical images being ultrasound images depicting different portions of the patient, and the ultrasound images forming video of the different portions;

providing the medical images to a machine learning model, wherein a forward pass through the machine learning model is computed, and wherein the machine learning model is trained to output for each input medical image, a bounding box about free fluid depicted in the input medical image and a confidence score associated with detection of the free fluid in the bounding box, the machine learning model being trained on a set of training images consisting essentially of ultrasound images that depict free fluid and that are each annotated with a ground-truth bounding box about the free fluid; and determining that the patient has free fluid based on analyzing output from the machine learning model, wherein the analyzing comprises, for an individual frame of the video in which the machine learning model outputs multiple bounding boxes:

maintaining the bounding box having a highest confidence score for the individual frame, determining a maximum confidence score across the frames of the video, and determining that the patient has free fluid in the respective portion based on the maximum confidence score exceeding a confidence score threshold, wherein the multiple bounded boxes in the video are presented, via an interactive user interface, based on the confidence score threshold being exceeded.

2. The method of claim 1, wherein the ultrasound images depict the left upper quadrant, right upper quadrant, or the patient's heart.

3. The method of claim 1, wherein the machine learning model is a convolutional neural network.

4. The method of claim 1, wherein a particular medical image has two bounding boxes assigned by the machine learning model, and wherein one of the bounding boxes associated with a higher confidence score is used to determine that the patient has free fluid.

5. The method of claim 1, wherein each portion of the patient is associated with a different confidence score threshold.

6. The method of claim 1, wherein the interactive user interface presents summary information including a graphical depiction of a particular medical image associated with a highest confidence value.

7. The method of claim 6, wherein the interactive user interface further presents information identifying a portion of the patient which has free fluid.

8. A system comprising one or more processors and non-transitory computer storage media storing instructions that when executed by the one or more processors, cause the one or more processors to perform operations comprising:

obtaining medical images associated with a patient, the medical images being ultrasound images depicting different portions of the patient, and the ultrasound images forming video of the different portions;

providing the medical images to a machine learning model, wherein a forward pass through the machine learning model is computed, and wherein the machine learning model is trained to output for each input medical image, a bounding box about free fluid depicted in the input medical image and a confidence score associated with detection of the free fluid in the bounding box, the machine learning model being trained on a set of training images consisting essentially of ultrasound images that depict free fluid and that are each annotated with a ground-truth bounding box about the free fluid; and determining that the patient has free fluid based on analyzing output from the machine learning model, wherein the analyzing comprises, for an individual frame of the video in which the machine learning model outputs multiple bounding boxes:

maintaining the bounding box having a highest confidence score for the individual frame, determining a maximum confidence score across the frames of the video, and determining that the patient has free fluid in the respective portion based on the maximum confidence score exceeding a confidence score threshold, wherein the multiple bounded boxes in the video are presented, via an interactive user interface, based on the confidence score threshold being exceeded.

9. The system of claim 8, wherein the ultrasound images depict the left upper quadrant, right upper quadrant, or the patient's heart.

10. The system of claim 8, wherein the machine learning model is a convolutional neural network.

11. The system of claim 8, wherein a particular medical image has two bounding boxes assigned by the machine learning model, and wherein one of the bounding boxes associated with a higher confidence score is used to determine that the patient has free fluid.

12. The system of claim 8, wherein each portion of the patient is associated with a different confidence score threshold.

13. The system of claim 8, wherein the interactive user interface presents summary information including a graphical depiction of a particular medical image associated with a highest confidence value.

14. The system of claim 13, wherein the interactive user interface further presents information identifying a portion of the patient which has free fluid.

15. Non-transitory computer storage media storing instructions that when executed by a system of one or more processors, cause the one or more processors to perform operations comprising:

obtaining medical images associated with a patient, the medical images being ultrasound images depicting different portions of the patient, and the ultrasound images forming video of the different portions;

providing the medical images to a machine learning model, wherein a forward pass through the machine learning model is computed, and wherein the machine learning model is trained to output for each input medical image, a bounding box about free fluid depicted in the input medical image and a confidence score associated with detection of the free fluid in the bounding box, the machine learning model being trained on a set of training images consisting essentially of ultrasound images that depict free fluid and that are each annotated with a ground-truth bounding box about the free fluid; and determining that the patient has free fluid based on analyzing output from the machine learning model, wherein the analyzing comprises, for an individual frame of the video in which the machine learning model outputs multiple bounding boxes:

maintaining the bounding box having a highest confidence score for the individual frame, determining a maximum confidence score across the frames of the video, and determining that the patient has free fluid in the respective portion based on the maximum confidence score exceeding a confidence score threshold, wherein the multiple bounded boxes in the video are presented, via an interactive user interface, based on the confidence score threshold being exceeded.

16. The computer storage media of claim 15, wherein a particular medical image has two bounding boxes assigned by the machine learning model, and wherein one of the bounding boxes associated with a higher confidence score is used to determine that the patient has free fluid.

17. The computer storage media of claim 15, wherein the interactive user interface presents summary information including a graphical depiction of a particular medical image associated with a highest confidence value.

* * * * *